Figure 1:
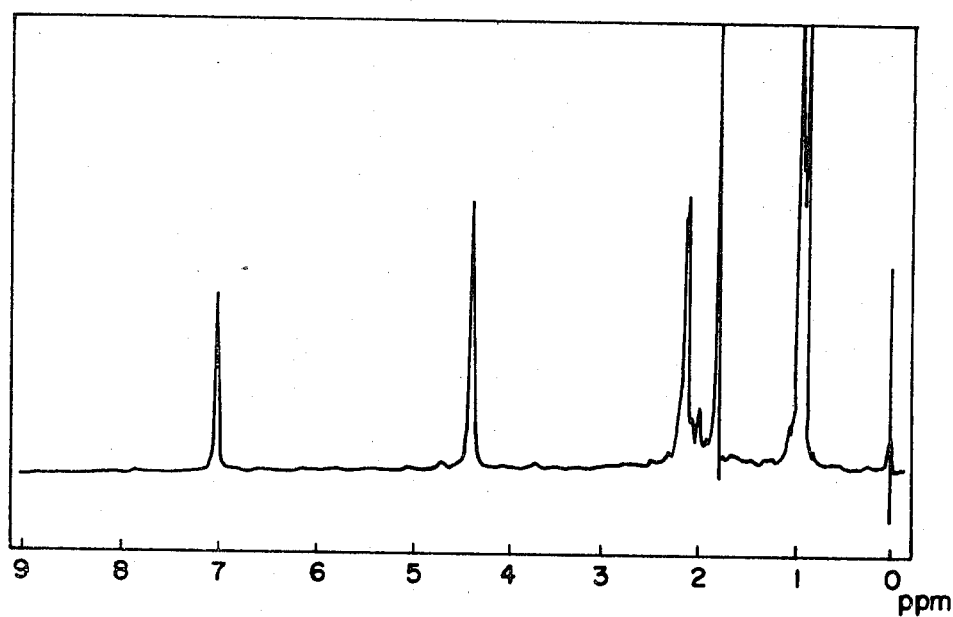

United States Patent [19]

Minato et al.

[11] 4,391,958
[45] Jul. 5, 1983

[54] ALDIMINES AND KETIMINES OF 1,3,5-(AMINOMETHYL)BENZENE OR CYCLOHEXANE AND THEIR USE AS CURING AGENTS FOR EPOXY AND POYLURETHANE RESINS

[75] Inventors: Ichiro Minato, Osaka; Koichi Shibata, Ashiya; Kimiya Fujinami, Takarazuka, all of Japan

[73] Assignee: Takeda Chemical Industries, Ltd., Osaka, Japan

[21] Appl. No.: 322,204

[22] Filed: Nov. 17, 1981

[30] Foreign Application Priority Data

Nov. 28, 1980 [JP] Japan ............................. 55-168377

[51] Int. Cl.³ .................... C08G 18/83; C08G 59/14; C07C 119/06
[52] U.S. Cl. ................................ 525/504; 528/60; 528/64; 528/122; 528/123; 564/248; 564/271
[58] Field of Search .................. 564/248, 271; 528/64, 528/121, 122, 123, 124, 60; 525/504

[56] References Cited

FOREIGN PATENT DOCUMENTS 972988 10/1964 United Kingdom .

*Primary Examiner*—Anton H. Sutto
*Assistant Examiner*—L. Hendriksen
*Attorney, Agent, or Firm*—Antonelli, Terry & Wands

[57] ABSTRACT

Disclosed is a novel triamine derivative, particularly a ketimine or aldimine derivative derived from a triamine and a ketone or an aldehyde, which has the following general formula:

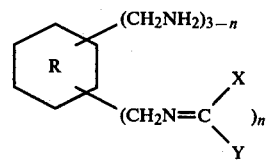

[wherein

R is

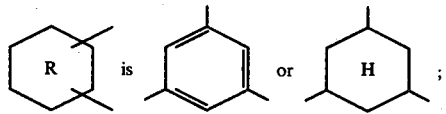

X is hydrogen or a hydrocarbon radical of 1 to 8 carbon atoms; Y is a hydrocarbon radical of 1 to 8 carbon atoms; X and Y, together with their neighboring carbon atom, may form a 5- to 7-membered aliphatic hydrocarbon ring; and n is an integer of 1, 2 or 3].

This novel triamine derivation is useful as a curing agent for epoxy resins or polyurethane resins.

13 Claims, 6 Drawing Figures

ALDIMINES AND KETIMINES OF 1,3,5-(AMINOMETHYL)BENZENE OR CYCLOHEXANE AND THEIR USE AS CURING AGENTS FOR EPOXY AND POYLURETHANE RESINS

The present invention relates to novel triamine derivatives and their use and more particularly to ketimine or aldimine derivatives which are derived from a triamine and ketones or aldehydes, which are useful as curing agents for epoxy resins or polyurethane resins.

Hitherto, various imine compounds have been known as curing agents for epoxy resins, for example, as disclosed in British Pat. No. 972,988 and U.S. Pat. No. 3,291,775. However, these compounds have a defect that when they are used as a curing agent at ambient temperatures, the resultant coating films are cloudy. Therefore, water is added to the curing composition and an aging time is demanded or the curing is effected by heating to obtain transparent coating film.

The present inventors have made intensive research on various derivatives of 1,3,5-tris(aminomethyl) benzene (MTA) or 1,3,5-tris(aminomethyl)cyclohexane (H$_6$MTA) and on their utilization. As a result, it has been found that the derivatives obtained by reacting said triamines with ketones or aldehydes possess excellent properties as a curing agent or curing regulating agent for epoxy resins, especially they can provide transparent coating film at ambient temperature. The finding was followed by further intensive investigation, which has culminated in the present invention.

Thus, the present invention covers the triamine derivatives of the general formula [I]:

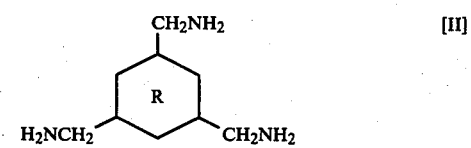

[wherein

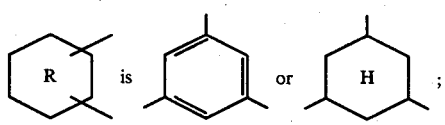

X is hydrogen or a hydrocarbon radical of 1 to 8 carbon atoms; Y is a hydrocarbon radical of 1 to 8 carbon atoms; X and Y, together with their neighboring carbon atom, may form a 5- to 7-membered aliphatic hydrocarbon ring; and n is an integer of 1, 2 or 3].

In the above general formula [I], as examples of the hydrocarbon radical of 1 to 8 carbon atoms represented by X, there may be mentioned saturated aliphatic hydrocarbons of 1 to 8 carbon atoms such as methyl, ethyl, isopropyl, propyl, butyl, isobutyl, pentyl, hexyl, heptyl and octyl, alicyclic hydrocarbons of 5 to 8 carbon atoms such as cyclopentyl and cyclohexyl, and a phenyl which may be or may not be substituted by lower alkyls such as methyl and ethyl and halogens such as chlorine.

The hydrocarbon of 1 to 8 carbon atoms represented by Y is the same hydrocarbon of 1 to 8 carbon atoms as defined above by X, and Y may be the same group as X, or different groups from X.

Further, X and Y, together with their neighboring carbon atom, may jointly form a 5- to 7-membered aliphatic hydrocarbon ring, and examples of such ring include 5- to 7-membered, saturated or unsaturated hydrocarbon rings such as cyclopentane, cyclohexane and cycloheptane.

Of the groups defined above by X and Y, the particularly preferred groups include saturated aliphatic hydrocarbon of 1 to 4 carbon atoms such as methyl, ethyl, propyl, isopropyl, butyl and isobutyl. Furthermore, a cyclohexane ring is preferable which is jointly formed by X and Y together with their adjacent carbon atom.

The derivative of the above general formula [I] can be produced by reacting a triamine of the general formula [II]:

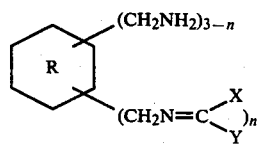

[wherein

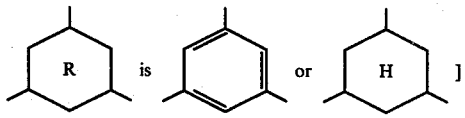

with a ketone or an aldehyde by use of the conventionally known procedure.

The triamines of the general formula [II] are novel substances and can be produced with the use of 1,3,5-tricyanobenzene, for example, as stated in Reference Examples 1 to 4 to be described later.

The ketones which are usable in the present invention are ketones of 3 to 17 carbon atoms, and use is made of aliphatic and aromatic ketones such as methyl ethyl ketone, methyl propyl ketone, methyl isopropyl ketone, methyl isobutyl ketone, acetone, ethyl butyl ketone, diethyl ketone, dipropyl ketone, dibutyl ketone, methyl cyclohexyl ketone, ethyl cyclohexyl ketone, acetophenone and benzophenone, and cyclic ketones such as cyclopentanone and cyclohexanone. Among these ketones, the preferred ones include methyl ethyl ketone, methyl isobutyl ketone, diisobutyl ketone, methyl butyl ketone, methyl propyl ketone, diethyl ketone, dibutyl ketone, methyl isopropyl ketone, ethyl butyl ketone and cyclohexanone.

And, the aldehydes are aldehydes of 2 to 9 carbon atoms, as exemplified by aliphatic and aromatic aldehydes such as acetaldehyde, propionaldehyde, butyl aldehyde, isobutyl aldehyde, valeraldehyde, isovaleraldehyde, pivalaldehyde, cyclohexyl aldehyde and benzaldehyde.

Among these aldehydes, the preferred ones include propionaldehyde, butyl aldehyde, isobutyl aldehyde, valeraldehyde, isovaleraldehyde, pivalaldehyde, benzaldehyde, etc.

Ketimines are more valuable than aldemine derivatives in offering the less curing time, though both derivatives give transparent coating film.

The triamine derivative [I] of the present invention can be produced by the procedure which comprises reacting a triamine of the general formula [II] with equivalent or excess of a ketone or an aldehyde without solvent or in solvent at temperatures of 0° C. to 200° C., and eliminating the resultant condensation water from the reaction system. The reaction can be advantageously guided by using inorganic acids such as hydrochloric acid and sulfuric acid, and catalysts such as phosphoryl chloride, boron trifluoride and titanium chloride in carrying out the present reaction.

The solvents which are usable in the present reaction include aliphatic hydrocarbons such as n-hexane, n-heptane and n-octane, alicyclic hydrocarbons such as cyclohexane, cyclooctane and cyclohexene, aromatic hydrocarbons such as benzene, toluene, xylene, cumene and mesitylene, alcohols such as methanol, ethanol, propanol, isopropanol, butanol, isobutanol, sec-butanol, t-butanol and cyclohexanol, ethers such as diethyl ether, tetrahydrofurane and dioxane, and heterocyclic aromatics such as pyridine, and other suitable solvent.

Of these solvents, furthermore, the solvents which distill as an azeotrope with the condensation water are of first choice as solvent for eliminating water out of the system. Among these, particularly, the preferred solvents include benzene, toluene, xylene, mesitylene, cumene, etc. In cases in which the ketone or aldehyde distills as an azeotrope with water, such ketone and aldehyde may be used in excess. Also, the reaction can be accelerated by allowing a dehydrating agent such as molecular sieve and caustic potash to exist in the reaction system. The progress of reaction can be recognized by following the distilled amount of the condensation water.

After the conclusion of the reaction, the solvent or excessive amount of the ketone or aldehyde can be removed by distillation, thereby yielding the product.

The derivatives of the present invention obtained by the above procedure can be used as a curing agent, particularly as a moisture-curing type curing agent or underwater curing agent, for epoxy resins or polyurethane resins. That is to say, the derivatives of the present invention, when being used as a curing agent, produce free amino groups due to water or moisture, and therefore the curing time can be freely regulated by controlling the water content of resins or the moisture in the air. Furthermore, the trifunctional derivatives (n=3) are of particular value as a curing agent for so-called one-can type resins and provide highly improved storage stability of the resins. In addition, the hardened materials cured by the derivatives of the present invention are excellent in various mechanical strengths, transparency, chemical resistance, heat distortion temperature, etc. As examples of the epoxy resins in which the derivatives of the present invention can be used as hardening agents, there may be mentioned various kinds of epoxy resins such as bisphenol-A type, bisphenol-F type, hydrogenated bisphenol-A and F types, alicyclic type, novolak type, polyoxyalkylene type, polyhydroxybenzene type, methylepichlorohydrin type and glycidylamine type epoxy resins, epoxy resins derived from dimer acid, phthalic acid, tetrahydrophthalic acid or p-oxybenzoic acid and epichlorohydrin, and halogen-containing epoxy resins.

The amount of triamine derivatives employed in the epoxy resin composition is such that, on hydrolysis of the derivatives to a triamine, there will be present one equivalent weight of epoxy group per amine hydrogen in the hydrolysis product. An excess or deflicency of triamine derivatives up to about 50% more or less than the amount corresponding to this stoichiometric proportion may be used.

The coating films prepared by curing the epoxy resin with the triamine derivatives of the present invention, particularly ketimines in which the number of n is 3 in the formula [I] are outstandingly characteristic in that the film have an appearance excellent in transparency in addition to the shortened curing time under the ambient conditions.

Further, the derivatives of the present invention can be changed to secondary amines by subjecting further to a reduction reaction.

With reference to the accompanying drawings, FIGS. 1, 2, 3, 4, 5 and 6 show the NMR spectrum of the derivative as obtained in Example 1, the IR spectrum of the derivative as obtained in Example 2, the IR spectrum of the derivative as obtained in Example 3, the NMR spectrum of the derivative as obtained in Example 4, the NMR spectrum of the derivative as obtained in Example 5 and the NMR spectrum of the derivative (the compound A) as obtained in Example 8, respectively.

Given below are the examples and reference examples to illustrate specifically the present invention.

REFERENCE EXAMPLE 1

Production of 1,3,5-tricyanobenzene

To 150 parts by weight of 33% aqueous oxalic acid solution was added 18.2 parts by weight of vanadium pentoxide, and the mixture was heated on a hot water bath at about 100° C. to dissolve vanadium pentoxide. The resultant solution was referred to as "A solution". Similarly, 20 parts by weight of chromium (VI) oxide was dissolved in 150 parts by weight of 33% aqueous oxalic acid solution, and the resultant solution was called "B solution". Both of the A and B solutions were mixed uniformly.

300 parts by weight of powder of anatase type titanium oxide burnt at 800° C. was added to the resultant mixed solution, and water was evaporated under stirring. The slurry-formed product thus obtained was molded by wet extrusion to cylindrical shape of 4 mm diameter and 5 mm length. The resultant moldings were dried at 100° C. for 15 hours and burnt at 500° C. for 4 hours to make a catalyst.

About 200 ml of the catalyst thus obtained was filled into a conventional fixed-bed reaction apparatus, and a mixed gas composed of 0.5 mole% of mesitylene, 7 mole% of ammonia and 92.5 mole% of air was reacted at a space velocity of 1000 hr$^{-1}$ (as converted to NTP), while maintaining the temperature of a bath for reaction tubes at 360° C. By the above procedure, there was obtained 1,3,5-tricyanobenzene (MTN) in a yield of 51.2 mole%.

REFERENCE EXAMPLE 2

Production of 1,3,5-tris(aminomethyl)benzene

In a 300 ml capacity, magnetic-stirring autoclave was sealed 15 g of 1,3,5-tricyanobenzene (MTN), together with 15 g of Raney nickel chromium catalyst (atomic ratio of Ni:Cr=49:1), 27 ml of methanol, 63 ml of m-xylene and 0.18 g of caustic soda. Hydrogen was charged under pressure into it at initial pressure of 100 kg/cm$^2$G, and the reaction was carried out at 100° C., whereby 0.59 mole of hydrogen was absorbed for 35 minutes. The catalyst was filtered out, and the solvent was distilled off, followed by distilling under reduced pressure, thereby yielding 12.8 g of colorless crystals of 1,3,5-tris(aminomethyl)-benzene (MTA). The substance exhibited melting point of 49° to 51° C. and boiling point of 136° to 139° C./0.4 mmHg.

REFERENCE EXAMPLE 3

Production of 1,3,5-tris(aminomethyl)cyclohexane

In a 300 ml capacity, magnetic-stirring autoclave was sealed 30 g of 1,3,5-tris(aminomethyl)benzene (MTA) as obtained in Reference Example 2, together with 3 g of 5% ruthenium-alumina catalyst (produced by Japan Engelhardt Co.), 60 g of water and 0.75 g of caustic soda, and high-pressure hydrogen of initial pressure of 120 kg/cm²G was charged under pressure into it. The reaction was allowed to proceed at 115° C. for 25 minutes, whereby 0.61 mole of hydrogen was absorbed.

The catalyst was filtered out, and the solvent was distilled off, followed by distilling under reduced pressure. Thus, 26.8 g of 1,3,5-tris(aminomethyl)cyclohexane ($H_6MTA$) was obtained. The $H_6MTA$ was a colorless, clear, low-viscous liquid of boiling point of 127°-8° C./1 mmHg.

REFERENCE EXAMPLE 4

Production of 1,3,5-tris(aminomethyl)cyclohexane

In a 300 ml capacity, magnetic-stirring autoclave was sealed 20 g of 1,3,5-tricyanobenzene as obtained in Reference Example 1, together with 80 ml of 25% aqueous ammonia, 300 mg of caustic soda and 4 g of commercially available 5% rhodiumalumina catalyst, and the reaction was allowed to proceed at 105° C. for 70 minutes under high-pressure hydrogen of initial pressure of 120 kg/cm²G, whereby 0.95 mole of hydrogen was absorbed. Thus, $H_6MTA$ having both its nitriles and nucleus reduced was obtained in a yield of 45%.

EXAMPLE 1

In a 200 ml flask were charged 5 g of MTA and 50 ml of toluene. The mixture was heated up to 50° C. to dissolve MTA, and then cooled down to 30° C., and 80 ml of a 20% toluene solution of methyl isobutyl ketone was quickly mixed with the solution under stirring.

Immediately, the mixture was subjected to heating and the condensation water, along with the solvent, was distilled off. At the time when about 70 ml of distillate was obtained, the residue was further concentrated by means of a rotary evaporator over a warm-water bath under reduced pressure of 30 mmHg to 2 mmHg, whereby there was obtained 12.3 g of a yellow liquid. FIG. 1 shows NMR spectrum ($CCl_4$) of the resultant product.

The IR spectrum of the product did not reveal a strong absorption due to N-H stretching vibration as observed in case of MTA itself of the raw material, and a strong absorption characteristic of a carbon-nitrogen double bond was anew observed at 1650 cm$^{-1}$.

The product was therefore confirmed to be N,N',N"-tris(4-methyl-2-pentylidene)-1,3,5-tris(aminomethyl)-benzene.

EXAMPLE 2

In a 200 ml Erlenmeyer flask was placed 50 ml of 20% toluene solution of methyl ethyl ketone, and to the solution was added under stirring 50 ml of 10% toluene solution of MTA melted by heating. Then, 25 g of molecular sieve 3A was added to the mixed solution, followed by allowing the solution to stand for 18 hours.

The molecular sieve was filtered out, and the filtrate was placed in a rotary evaporator. The solvent and excess of methyl ethyl ketone were distilled off, whereby there was obtained 7.6 g of a yellow liquid product showing a viscosity of 37 centipoise at 25° C.

Figure 2:
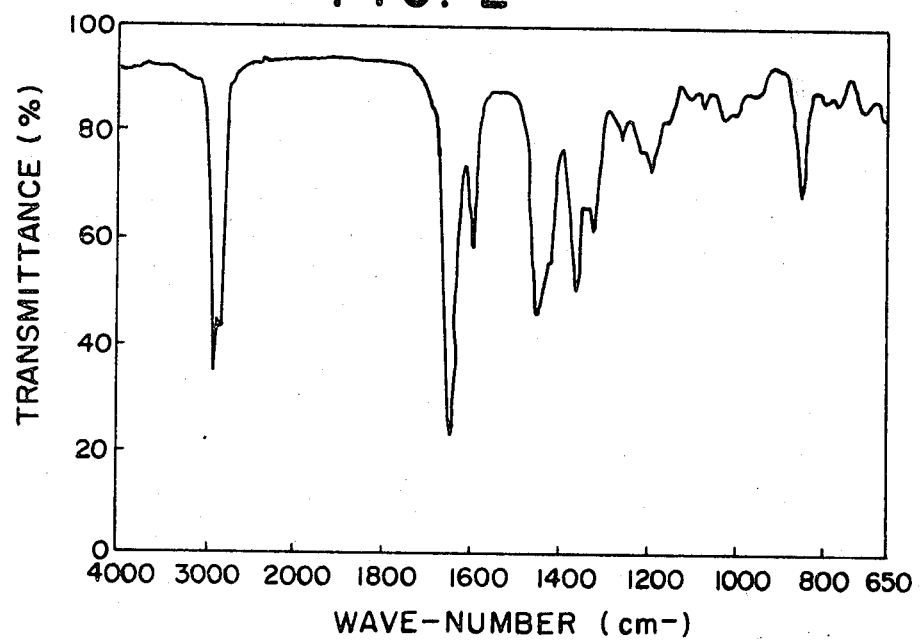

FIG. 2 shows the IR spectrum of the product. In the NMR spectrum ($CCl_4$), there appeared the absorption signals at 6.99 ppm(s), 4.37 ppm(s), 2.26 ppm(q), 1.82 ppm(s) and 1.09 ppm(t) with the intensity ratio of 1:2:2:3:3. The product was confirmed to be N,N',N"-tris(2-butylidene)-1,3,5-tris(aminomethyl)benzene.

EXAMPLE 3

The reaction was carried out under the same conditions as in Example 2, except that MTA was replaced by $H_6MTA$, and there was obtained 6.9 g of a slightly yellow liquid product.

Figure 3:
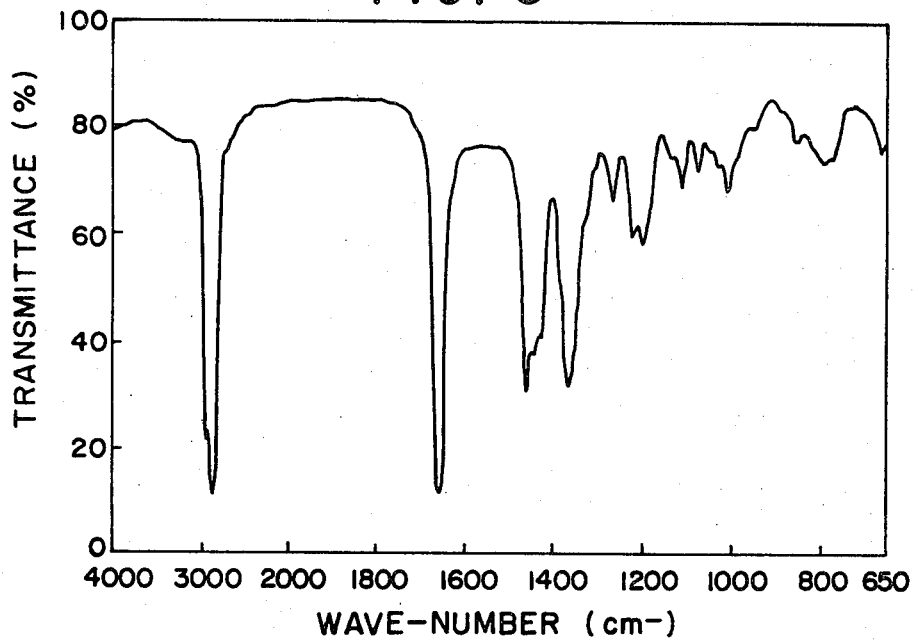

FIG. 3 illustrates the IR spectrum of the product.

The NMR spectrum showed the absorptions at 3.09 ppm(d) which is the signals due to methylene proton on the cyclohexane ring, and further showed complicated spectrum at 2.45 to 0.25 ppm composed of the peculiar absorption pattern due to the cyclohexane ring skeleton of $H_6MTA$ itself, which overlapped the absorption due to the methyl ethyl ketone residue at 2.23 ppm(q), 1.77 ppm(s) and 1.06 ppm(t).

The product was therefore confirmed to be N,N',N"-tris(2-butylidene)-1,3,5-tris(aminomethyl) cyclohexane.

EXAMPLE 4

Figure 4:
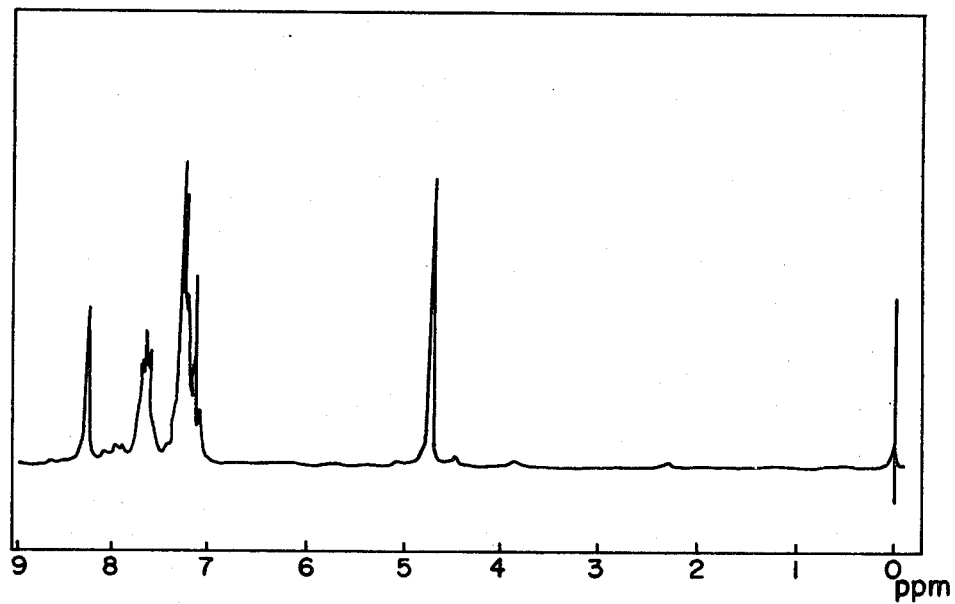

In a 500 ml Erlenmeyer flask was placed 100 ml of 5% toluene solution of MTA, and to the solution was quickly added 100 ml of 10% toluene solution of benzaldehyde under stirring. Immediately after the mixing, the solvent and excess of benzaldehyde were distilled off by means of a rotary evaporator at 60° C. under reduced pressure of 50 mm to 0.3 mmHg, and there was obtained 12.8 g of a yellow oily product. FIG. 4 shows the NMR spectrum of the product.

The IR spectrum of this product showed the characteristic absorptions at 2810 cm$^{-1}$, 2770 cm$^{-1}$ and 1630 cm$^{-1}$, and also displays the NMR spectrum ($CDCl_3$) as shown in FIG. 4. It was therefore confirmed that the product was N,N',N"-tris(benzylidene)-1,3,5-tris(aminomethyl)benzene.

EXAMPLE 5

Figure 5:
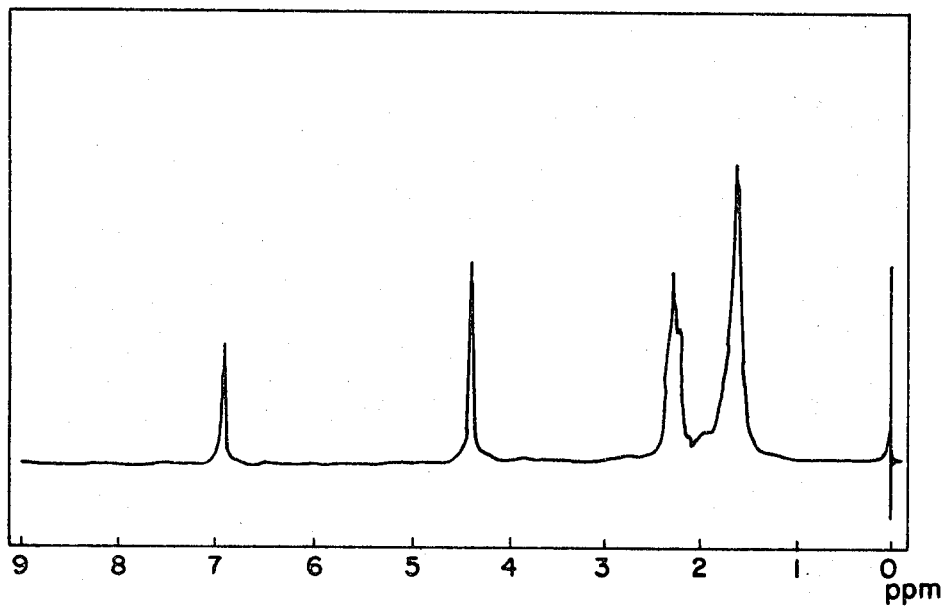

The reaction was carried out in the same manner as in Example 1, while using 65 ml of 20% toluene solution of cyclohexanone in place of the toluene solution of methyl isobutyl ketone, and there was obtained 12.0 g of a yellow liquid. FIG. 5 shows the NMR spectrum of the product.

The IR spectrum of this product revealed anew at 1648 cm$^{-1}$ a strong absorption due to the carbon-nitrogen double bond, in place of the absorption ascribed to the NH stretching vibration as observed in case of MTA itself, the raw material, and also displays the NMR spectrum as shown in FIG. 5. It was therefore confirmed that the product was N,N',N"-tris(cyclohexylidene)-1,3,5-tris(aminomethyl)benzene.

EXAMPLE 6

A 100 ml of 5% toluene solution of MTA was charged in a 300 ml, four-necked flask equipped with a reflux condenser and condensation water separating device and 80 ml of 50% toluene solution of diisobutyl ketone was added dropwise to the solution under stirring. Immediately after the dropwise addition, the mixed solution was warmed and refluxed for 3 hours, whereby the nearly theoretical amount of condensation water distilled away. The residue was concentrated by a rotary evaporator to remove the solvent and excess of diisobutyl ketone under reduced pressure, and there was obtained 16.1 g of a yellow liquid.

The IR spectrum of this product does not show the absorption due to the N-H but reveals absorptions at 2930 cm$^{-1}$, 1650 cm$^{-1}$, 1600 cm$^{-1}$, 1460 cm$^{-1}$, 1360 cm$^{-1}$, 1160 cm$^{-1}$ and 840 cm$^{-1}$, and the NMR spectrum (CCl$_4$) displays the absorption signals at 6.98 ppm(s), 4.36 ppm(s), 2.11 ppm(d), 2.00 ppm(s) and 0.89 ppm(d) with the intensity ratio of 1:2:4:2:12. It was therefore confirmed that the product is N,N',N''-tris(2,6-dimethyl-4-heptylidene)-1,3,5-tris (aminomethyl)benzene.

EXAMPLE 7

The reaction was carried out in the same manner as in Example 6, while replacing the MTA with H$_6$MTA, and there was obtained 15.7 g of a slightly yellow liquid.

The IR spectrum reveals the strong absorptions at 2930 cm$^{-1}$, 2880 cm$^{-1}$, 1655 cm$^{-1}$, 1460 cm$^{-1}$ and 1360 cm$^{-1}$, and the NMR spectrum (CCl$_4$) displays the absorption due to the methylene bound to the cyclohexane ring at 2.98 ppm(d) and, in the region from 2.40 ppm to 0.22 ppm, the peculiar absorption pattern due to the cyclohexane ring skeleton of the H$_6$MTA itself, which overlapped the absorptions due to the diisobutyl ketone residue. It was therefore confirmed that the product is N,N',N''-tris (2,6-dimethyl-4-heptylidene)-1,3,5-tris-(aminomethyl)cyclohexane.

EXAMPLE 8

The same reaction as in Example 2 was carried out, with the use of 28 ml of 10% toluene solution of methyl ethyl ketone, and molecular sieve 3A was added to the reaction mixture, followed by allowing the mixture to stand for 3 hours. Gas-chromatographic analysis indicated that the resultant product was a mixture of four kinds of compounds containing the unreacted MTA and N,N',N''-tris(2-butylidene)-1,3,5-tris(aminomethyl)benzene.

The mixture was subjected to fractional gas chromatography on a glass column of 1.2 m in length filled with the packing agent of 10% silicone SE-30 (Chromosorb W, AW-DMCS as the support), with the column temperature maintained at 220°C. and a nitrogen gas (50 m/min) used as the carrier gas, and there were obtained the liquid compounds A and B.

Figure 6:
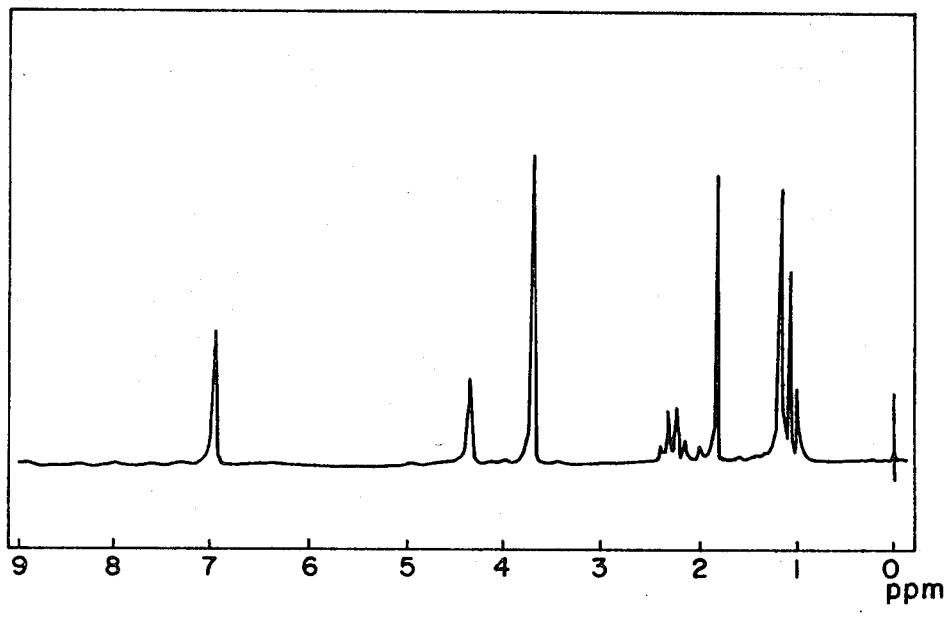

The compound A, which had the retention time of 3.24 minutes in the above gas chromatography, showed the IR spectrum revealing the absorptions ascribed to both the amino group and nitrogen-carbon double bond at 3350 cm$^{-1}$, 3260 cm$^{-1}$ and 1650 cm$^{-1}$ as well as the strong absorptions at 2960 cm$^{-1}$, 2900 cm$^{-1}$, 2850 cm$^{-1}$, 1600 cm$^{-1}$, 1450 cm$^{-1}$, 1360 cm$^{-1}$ and 840 cm$^{-1}$ and displays the NMR spectrum as shown in FIG. 6. It was therefore confirmed that the compound was N-2-butylidene-1,3,5-tris(aminomethyl)benzene.

The compound B, having the retention time of 7.05 minutes in the above gas chromatography, gives the IR spectrum which is very similar to that of the compound A (N-2-butylidene-1,3,5-tris(aminomethyl)benzene) but reveals the relatively weaker absorption ascribed to the amino group, and displays the NMR spectrum in which it was noted that: the spectra appear at almost the same positions as those of the compound A as illustrated in FIG. 6; intensity ratio of the absorption at 3.68 ppm (the methylene proton bound between the aromatic ring and primary amine) to the one at 4.34 ppm (the methylene bound between the aromatic ring and N=C bond) is 1:2 for the compound B in contrast to 2:1 for the compound A; and the whole absorption intensity ratio is in accordance with the proton ratio as the ketimine compound derived from one mole of MTA and two moles of methyl ethyl ketone. It was therefore confirmed that the compound B was N,N'-bis(2-butylidene)-1,3,5-tris-(aminomethyl)benzene.

EXAMPLE 9

By employing the ketimines as obtained in Examples 1 and 2 and an epoxy resin (produced by Shell Chemical; Epikote 828 with epoxide equivalent of 188.7), a coating film of 75μ was prepared on a glass plate in accordance with the procedure of JIS K-5400, "General testing method for paints". The curing was carried out in a laboratory at 21° C. of temperature and at 16.5° C. of wet-bulb temperature. The results are shown in Table 1.

TABLE 1

| Test Sample No. | Curing Agent* Kind | Curing Agent* Amount | Tack-free** After 10 hours | Tack-free** After 24 hours | Pencil Hardness After 24 hours | Pencil Hardness After 7 days | Resistance to solvent*** After 24 hours (Ethyl acetate) | Transparency Appearance | Transparency Transmittance (%)**** |
|---|---|---|---|---|---|---|---|---|---|
| a | Ketimine obtained in Example 1 | 36.3 | Δ | O | F | HB | O | Colorless Transparent | 91.3 |
| b | Ketimine Obtained in Example 2 | 28.9 | Δ | O | F | HB | O | Colorless Transparent | 89.5 |
| c | N,N'—bis (2-butylidene) methaxylylene diamine | 32.2 | Δ | O | HB | H | X | Opaque | 53.4 |

*parts per one hundred parts of resin
**The mark Δ means "slightly tacky". The mark O means "completely dry to the touch".
***The mark O means "good". The mark X means "poor".
****Transmittance of 75μ film was measured on Hitachi 124 Type Spectrophotometer Instrument at 600 mμ light.

EXAMPLE 10

By employing the curing agents as enumerated in the following Table 2 and an epoxy resin (Epikote 828 with an epoxide equivalent of 187.6), coating films of 75μ thick were prepared on a glass plate in accordance with the procedure of JIS K-5400, "General testing method for paints". The curing was carried out in a laboratory at 29.1° C. of temperature and at 26.9° C. of wet-bulk temperature. The results are shown in the following Table 2.

TABLE 2

| Test Sample No. | Curing Agents* Kind | Amount | Tack-free** After 14 hrs | Pencil Hardness After 24 hrs | Pencil Hardness After 7 days | Resistance to solvent*** After 24 hrs. (Ethyl acetate) | Transparency Appearance | Transmittance (%)**** |
|---|---|---|---|---|---|---|---|---|
| d | Ketimine obtained in Example 1 | 36.6 | O | HB | H | O | Colorless transparent | 91.7 |
| e | Ketimine obtained in Example 3 | 29.6 | O | H | 2H | O | Colorless transparent | 92.1 |
| f | Ketimine obtained in Example 5 | 36.0 | O | HB | H | O | Colorless transparent | 92.4 |
| g | HMDA—MEK | 29.9 | O | HB | H | X | Opaque | 34.2 |
| h | HMDA—MIBK | 37.4 | O | HB | H | X | Opaque | 44.1 |
| i | XDA—MIBK | 40.0 | O | HB | H | X | Opaque | 58.3 |

*Amount: parts per one hundred parts of resin
HMDA—MEK stands for N,N'—bis(2-butylidene)-hexamethylenediamine
HMDA—MIBK stands for N,N'—bis(4-methyl-2-pentylidene)-hexamethylenediamine
XDA—MIBK stands for N,N'—bis(4-methyl-2-pentylidene)-xylylenediamine
**The mark O means "completely dry to the touch".
***The mark O means "good"; The mark X means "poor".
****Transmittance of 75μ film was measured on Hitachi 124 Type Spectrophotometer at 600 mμ light.

The MTA and H₆MTA derivatives themselves are a low-viscotity liquid. Therefore, when mixed with the epoxy resin, they reduced greatly the viscosity of the mixture and it is unnecessary to use any diluent such as thinner. There was obtained the highly transparent coating film which was not obtainable from the known ketimine curing agents. Furthermore, the composition offered, the characteristic features of greatly improved processability; prolonged length of the pot life and shortened time for completing the curing reaction.

We claim:

1. A triamine derivative of the general formula:

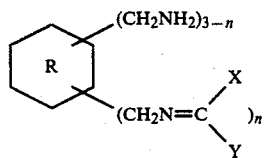

wherein

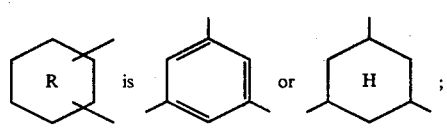

X is hydrogen or a hydrocarbon radical of 1 to 8 carbon atoms; Y is a hydrocarbon radical of 1 to 8 carbon atoms; X and Y, together with their neighboring carbon atom, may form a 5- to 7-membered aliphatic hydrocarbon ring; and n is an integer of 1, 2 or 3.

2. A triamine derivative according to claim 1, wherein

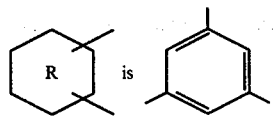

3. A triamine derivative of the general formula:

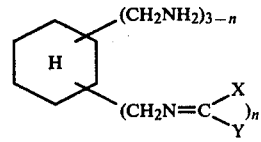

wherein X is hydrogen or a hydrocarbon radical of 1 to 8 carbon atoms; Y is a hydrocarbon radical of 1 to 8 carbon atoms; X and Y, together with their neighboring carbon atom, may form a 5- to 7-membered aliphatic hydrocarbon ring; and n is an integer of 1, 2 or 3.

4. A triamine derivative according to claim 1, wherein n is 3.

5. A triamine derivative according to claim 1, wherein X is a hydrocarbon radical of 1 to 8 carbon atoms.

6. A triamine derivative according to claim 1, wherein a hydrocarbon radical of 1 to 8 carbon atoms represented by X and Y is saturated aliphatic hydrocarbon of 1 to 8 carbon atoms.

7. A triamine derivative according to claim 6, wherein a hydrocarbon radical of 1 to 8 carbon atoms is saturated aliphatic hydrocarbon of 1 to 4 carbon atoms.

8. A triamine derivative according to claim 1, wherein either of X and Y is methyl and the other is ethyl or iso-butyl and n is 3.

9. A triamine derivative according to claim 1, wherein both of X and Y is iso-butyl and n is 3.

10. A triamine derivative according to claim 1, wherein X and Y, together with their neighboring carbon atom, jointly form a 5- to 7-membered, aliphatic hydrocarbon ring.

11. A triamine derivative according to claim 1, wherein X and Y, together with their neighboring carbon atom, jointly form a cyclohexane ring and n is 3.

12. Use of a triamine derivative according to claim 1 for curing an epoxy resin or a polyurethane resin.

13. An epoxy resin composition containing a triamine derivative according to claim 1 as a curing agent.

* * * * *